(12) United States Patent
Krapp et al.

(10) Patent No.: US 9,826,739 B2
(45) Date of Patent: Nov. 28, 2017

(54) NON-AQUEOUS ACTIVE INGREDIENT CONCENTRATES HAVING AN HERBICIDAL EFFECT

(75) Inventors: Michael Krapp, Altrip (DE); Rainer Berghaus, Speyer (DE); Matthias Bratz, Maxdorf (DE); Elmar Kibler, Haβloch (DE); Herve R. Vantieghem, Stutensee (DE)

(73) Assignee: BASF SE, Ludwigshafen (DE)

( * ) Notice: Subject to any disclaimer, the term of this patent is extended or adjusted under 35 U.S.C. 154(b) by 1357 days.

(21) Appl. No.: 12/376,320

(22) PCT Filed: Aug. 3, 2007

(86) PCT No.: PCT/EP2007/058091
§ 371 (c)(1),
(2), (4) Date: Feb. 4, 2009

(87) PCT Pub. No.: WO2008/015279
PCT Pub. Date: Feb. 7, 2008

(65) Prior Publication Data
US 2010/0227763 A1    Sep. 9, 2010

(30) Foreign Application Priority Data
Aug. 4, 2006  (EP) ..................................... 06118445

(51) Int. Cl.
A01N 43/80 (2006.01)
A01N 43/56 (2006.01)
A01N 43/10 (2006.01)
A01N 25/02 (2006.01)
A01N 25/30 (2006.01)

(52) U.S. Cl.
CPC ............. *A01N 43/56* (2013.01); *A01N 25/02* (2013.01); *A01N 25/30* (2013.01); *A01N 43/10* (2013.01); *A01N 43/80* (2013.01)

(58) Field of Classification Search
CPC ........ A01N 43/56; A01N 25/02; A01N 43/10; A01N 25/30; A01N 43/80
(Continued)

(56) References Cited

U.S. PATENT DOCUMENTS

| 5,846,907 A | 12/1998 | von Deyn et al. |
| 6,165,939 A | 12/2000 | Agbaje et al. |
| 6,534,444 B1 * | 3/2003 | Sievernich et al. ........... 504/128 |
| 2007/0123426 A1 | 5/2007 | Vantieghem et al. |

FOREIGN PATENT DOCUMENTS

| EP | 1023833 A2 | 8/2000 |
| GB | 2114566 A | 8/1983 |

(Continued)

OTHER PUBLICATIONS

The Pesticide Manual, 14th ed., Chapter 268 "Dimethenamid", pp. 341-343. (2006).
The Pesticide Manual, 14th ed., Chapter 831 "Topramezone", pp. 1047. (2006).

*Primary Examiner* — John Pak
*Assistant Examiner* — Andriae M Holt
(74) *Attorney, Agent, or Firm* — Drinker Biddle & Reath LLP

(57) ABSTRACT

The present invention relates to active compound concentrates having herbicidal action, comprising
a) from 10 to 100 g/l of at least one 4-benzoyl-substituted pyrazole compound of the formula I
in which

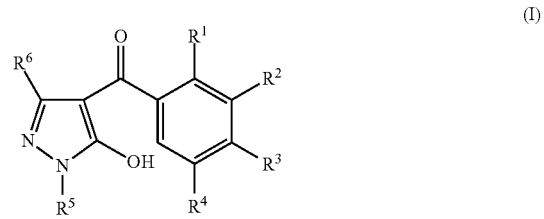

$R^1$, $R^3$ independently of one another are hydrogen, halogen, methyl, halomethyl, methoxy, halomethoxy, methylthio, methylsulfinyl or methylsulfonyl;

$R^2$ is a 5-membered heterocyclic radical which is unsubstituted or carries 1, 2, 3 or 4 substituents selected from the group consisting of halogen, $C_1$-$C_6$-alkyl, $C_1$-$C_4$-alkoxy, $C_1$-$C_4$-haloalkyl, $C_1$-$C_4$-haloalkoxy and $C_1$-$C_4$-alkylthio;

$R^4$ is hydrogen, halogen or methyl;

$R^5$ is $C_1$-$C_6$-alkyl, $C_3$-$C_6$-cycloalkyl or $C_3$-$C_6$-cycloalkylmethyl; and $R^6$ is hydrogen or $C_1$-$C_4$-alkyl;

or one of its agriculturally useful salts, b) from 200 to 700 g/l of 2-chloro-N-(2,4-dimethyl-3-thienyl)-N-(2-methoxy-1-methylethyl)acetamide, and c) from 10 to 200 g/l of at least one surfactant S selected from a mixture of at least one anionic surfactant and at least one nonionic surfactant, where the components a), b) and c) are present dissolved in a mixture of organic solvents consisting to at least 95% by weight, based on the solvent mixture, of d1) at least one aprotic polar organic solvent having a miscibility with water at 25° C. and 1 bar of at least 50 g/l, and d2) at least one organic solvent having a solubility in water at 25° C. and 1 bar of less than 5 g/l.

10 Claims, No Drawings

(58) Field of Classification Search
USPC .......................................................... 504/282
See application file for complete search history.

(56) References Cited

FOREIGN PATENT DOCUMENTS

| | | |
|---|---|---|
| JP | 2002506011 A | 2/2002 |
| WO | WO-96/26206 A1 | 8/1996 |
| WO | WO-99/65314 A1 | 12/1999 |
| WO | WO-2007/060146 A2 | 11/2005 |
| WO | WO-98/31681 A1 | 7/2008 |
| ZA | 98/00362 | 7/1999 |

* cited by examiner

NON-AQUEOUS ACTIVE INGREDIENT CONCENTRATES HAVING AN HERBICIDAL EFFECT

RELATED APPLICATIONS

This application is a stage application (under 35 U.S.C. §371) of PCT/EP2007/058091, filed Aug. 3, 2007, which claims benefit of European application 06118445.3, filed Aug. 4, 2006.

BACKGROUND OF THE INVENTION

The present invention relates to active compound concentrates having herbicidal action, comprising
a) at least one 4-benzoyl-substituted pyrazole compound of the formula I
in which

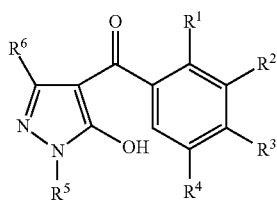

$R^1$, $R^3$ independently of one another are hydrogen, halogen, methyl, halomethyl, methoxy, halomethoxy, methylthio, methylsulfinyl or methylsulfonyl;
$R^2$ is a 5-membered heterocyclic radical which is unsubstituted or carries 1, 2, 3 or 4 substituents selected from the group consisting of halogen, $C_1$-$C_6$-alkyl, $C_1$-$C_4$-alkoxy, $C_1$-$C_4$-haloalkyl, $C_1$-$C_4$-haloalkoxy and $C_1$-$C_4$-alkylthio;
$R^4$ is hydrogen, halogen or methyl;
$R^5$ is $C_1$-$C_6$-alkyl, $C_3$-$C_6$-cycloalkyl or $C_3$-$C_6$-cycloalkylmethyl; and
$R^6$ is hydrogen or $C_1$-$C_4$-alkyl;
or one of its agriculturally useful salts, and
b) 2-chloro-N-(2,4-dimethyl-3-thienyl)-N-(2-methoxy-1-methylethyl)acetamide (dimethenamid).

The invention also relates to the use of such active compound concentrates for controlling unwanted vegetation, in particular for controlling graminaceous harmful plants.

Pure crops of agriculturally interesting useful plants are required for efficient and profitable practice of industrialized agriculture and for ensuring a consistent product quality. The selective sensitivity of different plant groups with respect to certain metabolic inhibitors or other cell toxins may be utilized for the targeted control of unwanted foreign vegetation (growth of harmful plants) on the areas under agricultural cultivation. Here, it is desirable in principle to enhance both the absolute efficacy and the specificity of the active compounds used (herbicides) against harmful plants.

The specificity and, within certain limits, the absolute efficacy can be enhanced by using combinations of a plurality of specific active compounds which attack at different points of the metabolism of the target plants. If the activity of the combination exceeds the sum of the individual activities significantly, this is referred to as synergism (occasionally also as superadditive effects).

The herbicidal action of the 4-benzoyl-substituted pyrazole compounds of the formula I is known from WO 96/26206 and WO 98/31681.

The herbicidal action of 2-chloro-N-(2,4-dimethyl-3-thienyl-N-(2-methoxy-1-methyl-ethyl)acetamide, also referred to as dimethenamid, is known from GB 2,114,566. Owing to the presence of two chiral elements (the chiral axis along the bond between the 3-position of the thiophene ring and the nitrogen atom of the amide group, and a center of asymmetry at carbon 1 of the 2-methoxy-1-methylethyl group), dimethenamid is a mixture of four stereoisomers. The stereoisomers of dimethenamid which, with respect to the asymmetric carbon atom of the 2-methoxy-1-methylethyl group, have the S-configuration are also referred to as S-isomer or as dimethenamid-P.

It is known from WO 99/65314 that the joint application of 4-benzoyl-substituted pyrazole compounds of the formula I and dimethenamid results in a herbicidal action which is increased compared to the application of the individual compounds. Formulations comprising both active compounds are not described in this publication.

What is desired, not least for reasons of practicability, are formulations comprising both the 4-benzoyl-substituted pyrazole compound of the formula I and dimethenamid in relatively concentrated form. Here, a number of problems have to be solved, in particular if the formulation comprises the active compounds in concentrated form. Since, prior to their application, such active compound concentrates are usually diluted with water, it has to be ensured that the concentrates can be diluted with water without any problems, and that the resulting aqueous dilution comprises the active compounds in relatively uniformly distributed form. However, frequently, especially concentrated active compound formulations (active compound concentrates) have, on prolonged storage, a tendency to undergo phase separation and/or to precipitate solids. On dilution with water, this then results in an uneven distribution of the active compounds in the aqueous dilution and/or inaccuracies when metering out the active compounds, which frequently eliminates the desired superadditive effect.

BRIEF SUMMARY OF THE INVENTION

Accordingly, it is an object of the present invention to provide a formulation for a mixture of 4-benzoyl-substituted pyrazole compounds of the formula I, as defined at the outset, and dimethenamid which comprises the two active compounds in relatively concentrated form.

According to a first subject matter of the present invention, this and further objects are achieved by a non-aqueous active compound concentrate, which comprises
a) from 10 to 100 g/l, in particular from 20 to 50 g/l, of at least one 4-benzoyl-substituted pyrazole compound of the formula I as defined above or one of its agriculturally useful salts,
b) from 200 to 700 g/l, in particular from 400 to 600 g/l, of 2-chloro-N-(2,4-dimethyl-3-thienyl)-N-(2-methoxy-1-methylethyl)acetamide, and
c) from 10 to 200 g/l, in particular from 20 to 100 g/l, of at least one surfactant S selected from a mixture of at least one anionic surfactant or surface-active compound and at least one nonionic surfactant or surface-active compound,
where the components a), b) and c) are present dissolved in a mixture of organic solvents consisting to at least 95% by weight, in particular at least 99% by weight, based on the solvent mixture, of d1) at least one aprotic polar organic solvent having a miscibility with water at 25° C. and 1 bar of at least 50 g/l, and
d2) at least one organic solvent having a solubility in water at 25° C. and 1 bar of less than 5 g/l, in particular less than 1 g/l.

Such non-aqueous active compound concentrates are particularly storage-stable and can be diluted without any problems with water to the desired application concentration. The aqueous active compound preparations prepared using the non-aqueous active compound concentrates moreover show little foaming (determined according to Ross-Miles). In addition, the aqueous active compound preparations obtained are particularly stable toward demixing (determined according to CIPAC MT). Furthermore, surprisingly, on application of the non-aqueous active compound concentrates according to the invention, an increased herbicidal action compared to the joint application of separate active compound formulations of active compounds of the formula I and dimethenamid is observed.

DETAILED DESCRIPTION OF THE INVENTION

According to a second subject matter of the present invention, the abovementioned objects are also achieved by an aqueous active compound concentrate, which comprises
a) from 10 to 100 g/l, in particular from 20 to 50 g/l, of at least one 4-benzoyl-substituted pyrazole compound of the formula I, as defined above,
b) from 200 to 700 g/l, in particular from 400 to 600 g/l, of 2-chloro-N-(2,4-dimethyl-3-thienyl)-N-(2-methoxy-1-methylethyl)acetamide, and
c) from 10 to 200 g/l, in particular from 20 to 100 g/l, of at least one surfactant S selected from nonionic surfactants and mixtures thereof with anionic surfactants,
where the components a) and b) are present in disperse form in an aqueous diluent.

The aqueous active compound compositions according to the invention, too, are storage-stable even at elevated temperature for a prolonged period of time and can be diluted without any problems with water to the desired application concentration. Moreover, they are distinguished by a low content of volatile organic hydrocarbons.

Here and below, alkyl and the alkyl moieties in alkylcarbonyl, alkoxy, alkylthio and alkylphenyl, are straight-chain or branched saturated hydrocarbon radicals. Correspondingly, alkenyl denotes straight-chain or branched hydrocarbon radicals which are monounsaturated. Haloalkyl and the haloalkyl moieties in haloalkoxy denote straight-chain or branched alkyl radicals in which 1 or more, for example 1, 2, 3, 4, 5 or else all, hydrogen atoms are replaced by halogen, in particular by chlorine or fluorine. Phenylalkyl denotes a phenyl radical which is connected via an alkyl group to the remainder of the molecule. Cycloalkyl denotes cyclic saturated hydrocarbon radicals. The prefix $C_n$-$C_m$ indicates in each case the number of possible carbon atoms.

Examples of alkyl are $C_1$-$C_4$-alkyl, such as methyl, ethyl, propyl, 1-methylethyl, butyl, 1-methylpropyl, 2-methylpropyl and 1,1-dimethylethyl, furthermore $C_1$-$C_6$-alkyl which, in addition to the radicals mentioned for $C_1$-$C_4$-alkyl, also includes pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, and also relatively long-chain alkyl radicals, such as n-heptyl, n-octyl, n-nonyl, isononyl, 2-ethylhexyl, n-decyl, isodecyl, 2-propylheptyl, dodecyl, tridecyl, isotridecyl, pentadecyl, lauryl, myristyl, palmityl, stearyl, behenyl and the like.

Alkylcarbonyl denotes an alkyl radical as mentioned above which is attached via a carbonyl group.

Alkoxy denotes an alkyl radical as defined above, which is attached via oxygen, in particular $C_1$-$C_4$-alkoxy, such as methoxy, ethoxy, propoxy, 1-methylethoxy, butoxy, 1-methylpropoxy, 2-methylpropoxy and 1,1-dimethylethoxy.

Haloalkyl denotes an alkyl radical as defined above in which one or more, for example 1, 2, 3, 4 or 5 or all, hydrogen atoms are replaced by halogen, in particular by fluorine or chlorine. Examples are fluoromethyl, chloromethyl, trifluoromethyl, difluoroethyl, 2,2,2-trifluoroethyl, pentafluoroethyl, 2-fluoro-1-methylethyl, 2,2,2-trifluoro-1-methylethyl, etc.

Cycloalkyl denotes a cyclic saturated hydrocarbon radical, such as, for example, cyclopentyl, cyclohexyl, cycloheptyl.

Phenylalkyl denotes a phenyl radical which is attached via an alkyl group, such as, for example, benzyl, 1- or 2-phenylethyl.

5-membered heterocyclic radicals are saturated, partially saturated or aromatic cycles which have 5 ring atoms (ring members) and which, in addition to the carbon atoms as ring members, have one or more, for example 1, 2, 3 or 4, heteroatoms, in particular 1 or 2 heteroatoms, as ring members, the heteroatoms preferably being selected from the group consisting of O, S and N. Examples of these radicals are 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, pyrrol-1-yl, pyrazol-1-yl, imidazol-1-yl, 1,2,3-triazol-1-yl and 1,2,4-triazol-1-yl.

The present invention relates in particular to active compound concentrates of compounds of the formula I in which $R^1$ and $R^3$ independently of one another are preferably halogen, methyl, methylthio, methylsulfinyl or methylsulfonyl. $R^2$ is in particular a radical selected from the group consisting of thiazol-2-yl, thiazol-4-yl, thiazol-5-yl, isoxazol-3-yl, isoxazol-4-yl, isoxazol-5-yl, 4,5-dihydroisoxazol-3-yl, 4,5-dihydroisoxazol-4-yl and 4,5-dihydroisoxazol-5-yl, where the radicals mentioned above are unsubstituted or may be substituted in the manner mentioned above and are in particular unsubstituted or may carry 1 or 2 methyl groups as substituents. $R^2$ is in particular selected from the group consisting of isoxazol-5-yl, 3-methylisoxazol-5-yl, 4,5-dihydroisoxazol-3-yl, 5-methyl-4,5-dihydroisoxazol-3-yl, 5-ethyl-4,5-dihydroisoxazol-3-yl and 4,5-dimethyl-4,5-dihydroisoxazol-3-yl. $R^4$ is in particular hydrogen. $R^5$ is in particular methyl. $R^6$ is in particular hydrogen or methyl. In particular, $R^1$ is chlorine, methyl or methylsulfonyl, $R^2$ is hydrogen or 4,5-dihydroisoxazol-3-yl, $R^3$ is chlorine or methyl-sulfonyl, $R^4$ is hydrogen, $R^5$ is methyl and $R^6$ is hydrogen or methyl.

In a particularly preferred embodiment of the invention, the active compound concentrates comprise a compound of the formula I in which $R^1$ is methyl, $R^2$ is 4,5-dihydroisoxazol-3-yl, $R^3$ is methylsulfonyl, $R^4$ is hydrogen, $R^5$ is methyl and $R^6$ is hydrogen, i.e. the component a) is 4-[2-methyl-3-(4,5-dihydroisoxazol-3-yl)-4-methylsulfonylbenzoyl]-1-methyl-5-hydroxy-1H-pyrazole (common name: topramezone).

Component b) of the active compound concentrates according to the invention can be employed as a racemic mixture of diastereomers or in the form of a mixture comprising one, two or three of the four diastereomers in enriched form. Particularly preferred components are the "S-isomer" of dimethenamid, i.e. dimethenamid-P, and also mixtures of the stereoisomers of this compound consisting predominantly of 1S-2-chloro-N-(2,4-dimethyl-3-thienyl)-N-(2-methoxy-1-methylethyl)acetamide. From among these, a particularly preferred component b) is pure dimethenamid-P or mixtures of the stereoisomers of this compound in which the ratio of "S-isomer" (dimethenamid-P, i.e. stereoisomers of dimethenamid having the S-configuration at the asymmetric carbon atom of the 2-methoxy-1-methylethyl group) to "R-isomer" (stereoisomers having the R-configuration at the asymmetric carbon atom of this group) is at least 8:2 and in particular at least 9:1.

In addition to the active compounds of the formula I and dimethenamid or dimethenamid-P, the non-aqueous active compound concentrates according to the invention comprise at least one surfactant suitable for stabilizing the active compound/solvent droplets formed on dilution with water in the aqueous diluent. According to the invention, this is a mixture of at least one anionic surfactant and at least one nonionic surfactant. The weight ratio of the at least one anionic surfactant to the at least one nonionic surfactant is typically in the range of from 1:10 to 10:1.

Suitable anionic surfactants are, in principle, all anionic surfactants typically used for stabilizing aqueous o/w emulsions. These are generally organic compounds having a hydrophobic radical, typically a hydrocarbon radical having 6 to 40, frequently 6 to 30 and in particular 8 to 22, carbon atoms and at least one functional group which, in aqueous media, is present in anionic form, for example a carboxylate, sulfonate, sulfate, phosphonate, phosphate, hydrogenphosphate or dihydrogenphosphate group. If appropriate, the anionic surfactants additionally have a poly-$C_2$-$C_3$-alkylene ether group, in particular a polyethylene oxide group having 1 to 50, in particular 2 to 30, $C_2$-$C_3$-alkylene oxide repeat units, in particular ethylene oxide repeat units.

Preferred anionic surfactants are those having at least one $SO_3$ group (sulfate and/or sulfonate) or one $PO_4$ group (phosphate group). From among these, preference is given to those anionic surfactants having at least one and in particular one aliphatic hydrocarbon radical having 8 to 22 carbon atoms or one araliphatic hydrocarbon radical having 10 to 26 carbon atoms. Such anionic surfactants are typically employed in the form of their alkali metal, alkaline earth metal or ammonium salts, in particular in the form of their sodium, potassium, calcium or ammonium salts. Here and below, the term "aliphatic" is meant to include alkyl, alkenyl and alkadienyl and preferably denotes alkyl. The term "aralkyl" denotes an aromatic hydrocarbon radical, such as phenyl or naphthyl, and preferably denotes phenyl having one or more, in particular one, alkyl group.

Examples of these are:

c.1. $C_8$-$C_{22}$-alkylsulfonates, such as laurylsulfonate and isotridecylsulfonate;

c.2. $C_8$-$C_{22}$-alkyl sulfates, such as lauryl sulfate, isotridecyl sulfate, cetyl sulfate and stearyl sulfate;

c.3. aryl- and $C_4$-$C_{20}$-alkylarylsulfonates, such as naphthalenesulfonate, dibutyl-naphthalenesulfonate, dodecyldiphenyl ether sulfonate, cumenesulfonate, nonylbenzenesulfonate, dodecylbenzenesulfonate, isotridecylbenzenesulfonate;

c.4. sulfates and sulfonates of fatty acids having preferably 8 to 22 carbon atoms and of fatty acid esters, for example sulfates and sulfonates of mono-, di- and triglycerides and of $C_1$-$C_{18}$-alkyl $C_8$-$C_{22}$-alkanoates;

c.5. sulfates of ethoxylated $C_8$-$C_{22}$-alkanols, for example the sulfates of ethoxylated lauryl alcohol, of ethoxylated isotridecanol, of ethoxylated $C_{16}$-$C_{18}$-alkanol mixtures, of ethoxylated stearyl alcohol, etc.;

c.6. sulfates of ethoxylated hydroxyaromatics, in particular sulfates of ethoxylated phenols, for example sulfates of ethoxylated $C_4$-$C_{22}$-alkylphenols, for example the sulfates of ethoxylated octylphenol, of ethoxylated nonylphenol, of ethoxylated dodecylphenol and of ethoxylated tridecylphenol, and also the sulfates of ethoxylated mono-, di- or tristyrylphenols;

c.7. mono- and diesters of phosphoric acid, including mixtures thereof with triesters of phosphoric acid, in particular the esters with $C_8$-$C_{22}$-alkanols, ethoxylated $C_8$-$C_{22}$-alkanols, with $C_4$-$C_{22}$-alkylphenols, with ethoxylated $C_4$-$C_{22}$-alkylphenols, with mono-, di- or tristyrylphenols, and also with ethoxylated mono-, di- or tristyrylphenols, and mixtures thereof;

c.8. mono- and di-$C_4$-$C_{22}$-alkyl esters of sulfosuccinic acid, such as dihexyl sulfosuccinate, dioctyl sulfosuccinate, and bis-2-ethylhexyl sulfosuccinate; and also c.9. condensates of naphthalenesulfonic acid or phenolsulfonic acid with formaldehyde and, if appropriate, urea.

Preferred anionic surfactants for the non-aqueous active compound concentrates according to the invention are those of groups c.1., c.2., c.3., c.5., c.6. and c.7., in particular those having an aliphatic hydrocarbon radical, i.e. an alkyl, alkenyl or alkadienyl radical, having 8 to 22 carbon atoms, and/or a $C_4$-$C_{22}$-alkylphenyl radical. In a particularly preferred embodiment of the present invention, the anionic surfactant comprises at least one surfactant from groups c.2. and c.3. and at least one further surfactant from group c.7.

Suitable nonionic surfactants are those having a poly-$C_2$-$C_3$-alkylene glycol ether group, hereinbelow also referred to as poly-$C_2$-$C_3$-alkoxylates or as poly-$C_2$-$C_3$-alkylene glycol ethers, and also polyethylene oxide/polypropylene oxide copolymers, in particular block copolymers. Hereinbelow, the terms poly(ethylene glycol-co-propylene glycol) and poly(ethoxylate-co-propoxylate) are used synonymously and denote compounds having a poly-$C_2$-$C_3$-alkylene glycol ether group constructed of ethylene oxide and propylene oxide repeat units.

Examples of preferred surfactants from the group of the poly-$C_2$-$C_3$-alkoxylates are in particular c.10. poly-$C_2$-$C_3$-alkylene glycol alkyl ethers, in particular polyethylene glycol alkyl ethers and poly(ethylene glycol-co-propylene glycol) alkyl ethers of straight-chain or branched $C_8$-$C_{22}$-alkanols, in particular polyethoxylates and poly(ethoxylate-co-propoxylates) of fatty alcohols and of oxo alcohols, for example polyethoxylates of lauryl alcohol, poly(ethoxylate-co-propoxylates) of lauryl alcohol, polyethoxylates of isotridecanol, poly(ethoxylate-co-propoxylates) of isotridecanol, polyethoxylates of cetyl alcohol, poly(ethoxylate-co-propoxylates) of cetyl alcohol, polyethoxylates of stearyl alcohol and poly (ethoxylate-co-propoxylates) of stearyl alcohol, and also the corresponding $C_1$-$C_4$-alkyl ethers, in particular the methyl ethers, and the $C_1$-$C_4$-alkanoates of these compounds;

c.11. poly-$C_2$-$C_3$-alkylene glycol aryl ethers, in particular polyethoxylates and poly(ethoxylate-co-propoxylates) of hydroxyaromatics, for example of $C_1$-$C_{22}$-alkylphenols, such as, for example, the polyethoxylates and poly (ethoxylate-co-propoxylates) of nonylphenol, decylphenol, isodecylphenol, dodecylphenol, isotridecylphenol, of mono-, di- or tristyrylphenol and mixtures thereof, and also the $C_1$-$C_4$-alkyl ethers, in particular the methyl ethers, and the $C_1$-$C_4$-alkanoates of the abovementioned ethoxylates and poly(ethoxylate-co-propoxylates);

c.12. poly-$C_2$-$C_3$-alkoxylates, in particular polyethoxylates, of $C_8$-$C_{22}$-alkyl glucosides and poly-$C_2$-$C_3$-alkoxylates, in particular polyethoxylates, of $C_8$-$C_{22}$-alkyl polyglucosides;

c.13. poly-$C_2$-$C_3$-alkoxylates, in particular polyethoxylates and poly(ethoxylate-co-propoxylates) of fatty amines, in particular polyethoxylates and poly(ethoxylate-co-propoxylates) of stearylamine, tallow fatty amine, oleylamine and coco fatty amine;

c.14. poly-$C_2$-$C_3$-alkoxylates, in particular polyethoxylates of fatty acids, for example polyethoxylates of stearic acid, lauric acid, oleic acid, myristic acid, of mixtures of the fatty acids mentioned above;

c.15. polyethoxylated fats and oils, for example polyethoxylates of coco oil, palm kernel oil, tallow oil, palm oil, rapeseed oil, sunflower oil or castor oil; and also c.16. poly-$C_2$-$C_3$-alkoxylates, in particular polyethoxylates, of sorbitan fatty esters, for example polyethoxylates of sorbitan mono-, di- or trioleate and mixtures thereof.

In the polyethoxylates mentioned above, the degree of ethoxylation (mean number of repeat units derived from ethylene oxide in the molecule) is typically in the range of from 2 to 100, in particular in the range of from 3 to 50 and especially in the range of from 5 to 40. In the (poly) ethoxylate-co-propoxylates, the mean number of repeat units derived from ethylene oxide is generally from 1 to 50, in particular from 2 to 40 and especially from 3 to 30, and the mean number of repeat units derived from propylene oxide is from 1 to 50, in particular from 2 to 40 and especially from 2 to 30.

The preferred nonionic surfactants also include copolymers, in particular block copolymers, of ethylene oxide and propylene oxide (hereinbelow referred to as EO/PO copolymers). These are to be understood as meaning oligomeric or polymeric polyether compounds constructed predominantly, i.e. to at least 90% by weight, of repeat units EO ($CH_2$—$CH_2$—O) and PO (=$CH_2$—$CH(CH_3)$—O). From among these, preference is given to ethylene oxide/propylene oxide block copolymers in which the number of PO blocks and EO blocks is preferably 2 or, in particular, 3. Especially preferred are triblock copolymers of the formulae below

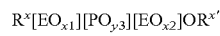

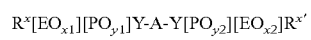

Here, the unit $[PO_{y1}]A[PO_{y2}]$ is considered to be a PO block. In the formulae, $R^x$ and $R^{x'}$ independently of one another are hydrogen or $C_1$-$C_{10}$-alkyl, and EO, PO are as defined above. Independently of one another, the indices x1 and x2 have a value in the range of from 2 to 100, in particular from 4 to 50. Independently of one another, the indices y1 and y2 have a value in the range of from 2 to 100, in particular from 4 to 50. The index y3 typically denotes a value of from 2 to 160, in particular a value of from 4 to 100 and especially of from 10 to 80. The index x3 typically denotes a value of from 4 to 200, in particular a value of from 10 to 100 and especiallly of from 10 to 80. A is $C_4$-$C_{10}$-alkanediyl or $C_5$-$C_{10}$-cycloalkanediyl. Y is oxygen or a radical NR in which R is hydrogen, $C_1$-$C_4$-alkyl or a group of the formula $R^x[EO_{x1}][PO_{y1}]$. The number-average molecular weight of the EO/PO copolymers is preferably in the range of from 300 to 10 000 dalton, in particular in the range of from 500 to 5000 dalton. The percentage of EO repeat units is typically in the range of from 10 to 90% by weight, in particular in the range of from 20 to 80% by weight, and the percentage of PO repeat units is typically in the range of from 10 to 90% by weight, in particular in the range of from 20 to 80% by weight, in each case based on the total weight of the EO/PO copolymer.

In a preferred embodiment of the present invention, the nonionic surfactant comprises at least one surfactant of the group of the poly-$C_2$-$C_3$-alkoxylates, in particular from groups c.10, c.11 and/or c.15., and/or a mixture of one or more, for example 1 or 2, poly-$C_2$-$C_3$-alkoxylates with an EO/PO copolymer and especially an EO/PO block copolymer.

Furthermore, as component D1, the active compound concentrates according to the invention comprise at least one aprotic polar organic solvent having a miscibility with water at 25° C. and 1 bar of at least 50 g/l, in particular at least 100 g/l, and which is in particular completely miscible with water. These include:

amides, N—$C_1$-$C_4$-alkylamides and N,N—$C_1$-$C_4$-dialkylamides of aliphatic carboxylic acids having 1 to 12, in particular 1 to 6, carbon atoms, in particular the amides, N—$C_1$-$C_2$-alkylamides and N,N—$C_1$-$C_2$-dialkylamides of formic acid, of acetic acid, of propionic acid, of valeric acid and of capronic acid, such as formamide, dimethylformamide, acetamide, propionamide, N,N-dimethylacetamide, dimethylpropionamide and dimethylvaleramide;

sulfones and sulfoxides, such as sulfolane and dimethyl sulfoxide, $C_1$-$C_3$-alkylnitriles, such as acetonitrile and propionitrile;

5-, 6- and 7-membered lactams which may have an N—$C_1$-$C_4$-alkyl group, in particular a methyl group, at the nitrogen atom, for example pyrrolidone, N—$C_1$-$C_4$-alkylpyrrolidones, such as N-methylpyrrolidone, N-ethylpyrrolidone, N—$C_1$-$C_4$-alkylvalerolactams, such as N-methylvalerolactam, and also 5- or 6-membered lactones, such as γ-butyrolactone.

Preferred aprotic polar solvents are the amides mentioned above and the N,N—$C_1$-$C_4$-dialkylamides of aliphatic $C_1$-$C_6$-carboxylic acids, in particular the amides and dimethylamides of these carboxylic acids, especially of formic acid, of acetic acid, of propionic acid and of valeric acid, furthermore N—$C_1$-$C_4$-alkylpyrrolidones, especially N-methylpyrrolidone, N—$C_1$-$C_4$-alkylvalerolactams, especially N-methylvalerolactam, and also dimethyl sulfoxide, and mixtures thereof.

The aprotic polar organic solvent comprises in particular at least 80% by weight, based on the total amount of aprotic polar organic solvent in the formulation, of one of the abovementioned preferred aprotic polar solvents, in particular dimethyl sulfoxide and/or N-methylpyrrolidone.

Furthermore, the non-aqueous active compound concentrate according to the invention comprises at least one organic solvent which, at 25° C. and 1 bar, has a solubility in water of less than 5 g/l, in particular less than 1 g/l. These include in particular hydrocarbon solvents and $C_1$-$C_{10}$-alkyl esters of fatty acids. The hydrocarbon solvents are a hydrocarbon liquid at room temperature or a liquid hydrocarbon mixture as typically used for preparing emulsifiable active compound concentrates. Suitable hydrocarbons are alkanes having preferably 6 to 14 carbon atoms, cycloalkanes having optionally 1, 2, 3 or 4 $C_1$-$C_4$-alkyl groups and preferably a total of 6 to 14 carbon atoms, aromatic hydrocarbons, such as benzene, naphthalene, mono-, di- and tri-$C_1$-$C_4$-alkyl-substituted benzene, in particular toluene, xylenes, mesitylene, cumene and also $C_1$-$C_4$-alkyl-substituted naphthalene and also mixtures of the hydrocarbons mentioned above. Preference is given in particular to hydrocarbons and hydrocarbon mixtures having a content of aromatic hydrocarbons of at least 50% by weight and in particular at least 80% by weight. Preference is furthermore given to hydrocarbons and hydrocarbon mixtures whose boiling point or whose minimum boiling point according to ASTM D86 is at least 150° C., in particular 180° C. and especially at least 200° C. Such hydrocarbons and hydrocarbon mixtures are familiar to the person skilled in the art and commercially available, for example under the names Shellsol® A of Shell AG and under the name Solvesso®, for example under the names Solvesso® 100, Solvesso®150, Solvesso®150 ND, Solvesso®200, Solvesso®200 ND and Solvesso®200 S.

The alkyl esters of fatty acids include in particular the $C_1$-$C_6$-alkyl esters and especially the methyl esters of aliphatic saturated or unsaturated $C_6$-$C_{20}$-monocarboxylic acids, in particular the esters of capronic acid, enanthic acid, caprylic acid, pelargonic acid, caprinic acid, undecanoic acid, lauric acid, myristic acid, palmitic acid, stearic acid, oleic acid or palmitoleic acid, and also mixtures of fatty acid $C_1$-$C_6$-alkyl esters, in particular fatty acid methyl esters, as obtained by transesterification of native triglycerides with $C_1$-$C_6$-alkanols, especially methanol, for example soybean oil methyl ester, rapeseed oil methyl ester, palmitic acid methyl ester, stearic acid methyl ester and oleic acid methyl ester, and mixtures thereof.

Preference is given to hydrocarbons solvents.

In the non-aqueous active compound concentrates according to the invention, the weight ratio of aprotic polar organic solvent to hydrocarbon solvent is preferably from 1:10 to 10:1, in particular from 1:5 to 5:1.

The total amount of organic solvent, i.e. aprotic polar organic solvent and hydrocarbon solvent, is typically in the range of from 200 to 800 g/l and in particular in the range of from 300 to 600 g/l.

The non-aqueous active compound concentrates according to the invention may furthermore comprise customary components typically used in emulsion concentrates of herbicidally active compounds. These include, for example, antifoams and preservatives. Preferably, the percentage of these components does not exceed 5% by weight and in particular 1% by weight, based on the total weight of the non-aqueous active compound concentrate.

The non-aqueous active compound concentrates according to the invention can be prepared analogously to the preparation of conventional emulsifiable concentrates. Preferably, a solution of the at least one 4-benzoyl-substituted pyrazole compound I in at least part of the aprotic polar solvent is first prepared. If appropriate, the preparation of this solution is carried out with heating; however, temperatures of 80° C. should preferably not be exceeded. In general, the solution is prepared at ambient temperature or in the range of from 10 to 50° C. The other components of the formulation are then added to the solution obtained in this manner, it being possible to add dimethenamid or dimethenamid-P in dissolved form or as a solid. Frequently, the hydrocarbon solvent, dimethenamid or dimethenamid-P, the surfactants and, if appropriate, further components are added successively to the solution of the compound of the formula I in the aprotic polar organic solvent, and the mixture obtained in this manner is homogenized using suitable apparatus, for example using suitable stirrers, dissolvers and the like, until a clear homogeneous mixture is obtained. The addition of hydrocarbon solvent, dimethenamid or dimethenamid-P, surfactants and, if appropriate, further components and the homogenization are typically carried out at ambient temperature or in the range of from 10 to 50° C. The active compound concentrate obtained in this manner can then be formulated and packaged in a customary manner.

A second subject matter of the present invention relates to an aqueous active compound concentrate in accordance with the above definition.

In the aqueous active compound concentrates according to the invention, the active compounds the formula I and dimethenamid are present in disperse form, i.e. in the form of finely distributed particles. Here, the term "particle" embraces both solid active compound particles and liquid active compound droplets. Without subscribing to any theory, it is assumed that the predominant part of the at least one active compound of the formula I is present in the form of solid active compounds particles, whereas the predominant part of the dimethenamid is presumably present in the form of oily droplets. The particle size of the active compound particles (solid active compound particles and droplets) is typically not more than 50 μm, in particular 20 μm and especially 10 μm (the $d_{90}$ value, i.e. the value which is exceeded by at most 10% by weight of the active compound particles present in the concentrate). The weight-average particle size ($d_{50}$ value) is typically in the range of from 0.1 to 10 μm and in particular in the range of from 0.5 to 5 μm. The values given here refer to the values determined by quasi-elastic light scattering using dilute aqueous samples of the active compound concentrates (rate of dilution 1:20 to 1:200).

According to the invention, the aqueous active compound concentrates comprise at least one nonionic surfactant or a mixture thereof with at least one anionic surfactant. According to the invention, the total concentration of surfactants, i.e. the concentration of nonionic surfactant plus any anionic surfactants present, if appropriate, is in the range of from 10 to 200 g/l, in particular in the range of from 15 to 150 g/l and especially in the range of from 20 to 100 g/l. If the aqueous active compound concentrates according to the invention comprise a mixture of at least one nonionic surface-active compound and at least one anionic surface-active compound, the weight ratio of nonionic surfactant to anionic surfactant is preferably from 100:1 to 10:1, in particular from 50:1 to 5:1.

Suitable nonionic surfactants are, in principle, all nonionic surfactants mentioned above for the non-aqueous active compound concentrates, preferably nonionic surfactants from the group of the poly($C_2$-$C_3$-alkoxylates), for example substances from groups c.10. to c.16, in particular nonionic surfactants from groups c.10, c.11 and c.12. From among these, particular preference is given to the poly (ethoxylate-co-propoxylates) of groups c.10. and c.11. Such compounds can be described by the general formula (III)

in which
R is $C_{10}$-$C_{22}$-alkyl, $C_8$-$C_{22}$-alkylphenyl, mono-, di- or tristyryl,
R' is hydrogen, $C_1$-$C_{10}$-alkyl, benzyl, formyl or $C_1$-$C_{10}$-alkylcarbonyl, in particular hydrogen,
A is $CH(CH_3)CH_2$,
E is $CH_2CH_2$,
x is a number in the range of from 1 to 30, in particular from 1 to 10, and
y is a number in the range of from 2 to 50, in particular from 2 to 30.

Suitable nonionic surfactants in particular also include ethylene oxide/propylene oxide copolymers as already mentioned in connection with the non-aqueous active compound concentrates, in particular the triblock copolymers mentioned there.

In a preferred embodiment, the nonionic surfactant comprises at least one nonionic surfactant of groups c.10 to c.16, in particular of groups c.10. and/or c.11, and especially at least one nonionic surfactant of the general formula III, and also, if appropriate, at least one EO/PO copolymer, especially an EO/PO block copolymer of the type described above. In this embodiment, the weight ratio of the at least one surfactant of groups c.10. to c.16 to the EO/PO copolymer(s) is typically in the range of from 100:1 to 1:1 and especially in the range of from 50:1 to 5:1.

In addition, the aqueous active compound concentrate according to the invention may also comprise one or more anionic surfactants. In principle, suitable surfactants are all those which have been mentioned above in connection with the non-aqueous active compound concentrates, in particular anionic surfactants of groups c.1 to c.9. and especially anionic surfactants of group c.9.

The aqueous active compound concentrates according to the invention may additionally also comprise further substances which are not directly relevant to the aim of the compositions, but which improve their applicability and/or practical properties. Examples of these are in particular
viscosity-regulating substances (thickeners),
preservatives,
antifoams,
agents for adjusting the pH,
antifreeze agents.
Such substances are familiar to the person skilled in the art. The total amount of such substances will generally not exceed 10% by weight (=about 100 g/l), based on the active compound concentrate, and is typically in the range of from 0.1 to 10% by weight (=1 to 100 g/l), based on the total weight of the active compound concentrate.

The viscosity-modifying additives (thickeners) include in particular compounds which are known to impart pseudoplastic flow behavior to aqueous formulations, i.e. high viscosity in the state of rest and low viscosity in the state of motion. Suitable are, in principle, all compounds used for this purpose in aqueous active compound concentrates. Mention may be made, for example, of inorganic substances, such as bentonite or attapulgite (for example Attaclay® from Engelhardt), and organic substances, such as polysaccharides and heteropolysaccharides, such as Xanthan Gum® (Kelzan® from Kelco), Rhodopol® 23 (Rhone Poulenc) or Veegum® (from R.T. Vanderbilt), with Xanthan-Gum® preferably being used. The amount of viscosity-modifying additives is frequently from 0.1 to 5% by weight, based on the total weight of the active compound concentrate.

Suitable antifoams are, for example, silicone emulsions (Silikon® SRE, from Wacker, or Rhodorsil®, from Rhodia), long-chain alcohols, fatty acids, defoamers of the type of aqueous wax dispersions, solid defoamers ("compounds"), organofluorine compounds and mixtures thereof known for this purpose. The amount of antifoam is typically from 0.1 to 3% by weight, calculated as foam-active substance and based on the total weight of the active compound concentrate.

Examples of preservatives are those based on isothiazolones, for example Proxel® from ICI or Acticide® RS from Thor Chemie or Kathon® MK from Rohm & Haas. The amount of preservatives, if present, is typically from 0.05 to 0.5% by weight, based on the total weight of the active compound concentrate.

Suitable antifreeze agents are liquid alkanols, such as methanol, ethanol, isopropanol, n-butanol, polyols, for example ethylene glycol, propylene glycol or glycerol. The amount of antifreeze agents, if present, is generally from 1 to 10% by weight, based on the total weight of the active compound concentrate.

The aqueous active compound concentrates according to the invention can be prepared analogously to known processes for preparing suspension concentrates or suspoemulsion concentrates comprising at least two different active compounds.

To this end, in general, an aqueous suspension of the at least one active compound of the formula I and, separately therefrom, an aqueous suspension or emulsion of dimethenamid are prepared, and the two suspensions or the suspension and the emulsion are combined to give the aqueous active compound concentrate according to the invention. The suspensions of the compounds I, like the suspensions or emulsions of dimethenamid, can be prepared analogously to the preparation of aqueous suspension concentrates of organic crop protection agents.

For example, a first aqueous suspension of the at least one active compound of the formula I can be prepared by initially preparing an aqueous slurry of the at least one active compound of the formula I, followed by grinding to achieve the desired particle size. In general, the aqueous slurry comprises part of the surfactants present in the concentrate, for example an ethylene oxide/propylene oxide copolymer and, if appropriate, an anionic surfactant, and also, if appropriate, defoamers and, if appropriate, part or all of the antifreeze agent. Water and further components, for example the residual amount of antifreeze agent, thickener and biocide, can then be added to the aqueous suspension, obtained in this manner, of the at least one active compound I, the auxiliaries typically being added in the form of an aqueous solution.

The aqueous emulsion or suspension of dimethenamid can be prepared in a manner known per se analogously to the preparation of aqueous concentrates of dimethenamid. Frequently, an aqueous solution comprising at least part of the surfactants, in particular at least one surfactant of the formula III, is initially charged, and dimethenamid is suspended or emulsified therein, if appropriate with heating. The aqueous initial charge may additionally comprise part or all of the further components of the aqueous active compound concentrate, for example thickener, biocide, part of the antifreeze agent and, if appropriate, defoamer.

The suspension of the at least one active compound of the formula I is then combined by mixing with the aqueous suspension or emulsion of the dimethenamid, for example with stirring, giving the finished formulation. It is, of course, also possible to add part of the optional additives subsequently thereto, preferably in the form of an aqueous solution.

The non-aqueous active compound concentrates according to the invention, like the aqueous active compound concentrates according to the invention, are suitable in a manner known per se for controlling unwanted vegetation. The active compound concentrates according to the invention are particularly suitable for controlling unwanted vegetation on non-crop areas, especially at high application rates. In crops such as cereals, for example wheat, rye, barley, oats, millet and triticale, and also in corn, they act against broad-leaved weeds and weed grasses without causing any significant damage to the crop plants. This effect is mainly observed at low rates of application.

Depending on the application method in question, the active compound concentrates according to the invention can additionally be employed in a further number of crop plants for eliminating unwanted plants.

In addition, the active compound concentrates can also be used in crops which tolerate the action of herbicides owing to breeding, including genetic engineering methods.

The active compound concentrates are generally applied in the form of an aqueous spray liquor. To this end, the active compound concentrates according to the invention are, depending on the application rate, diluted with water to a multiple of their volume, for example 10- to 10 000-fold, in particular 20- to 1000-fold. The active compound concentration in the spray liquor is then typically in the range of from 10 mg/l to 10 g/l.

Application may be by the pre-emergence method, by the post-emergence method or together with the seed of a crop plant. It is also possible to apply the active compounds of the formula I and dimethenamid or dimethenamid-P present in the active compound concentrates using the active compound concentrates according to the invention by treating seed of a crop plant with an aqueous dilution of the active compound concentrates and sowing the seed treated in this manner. If the active compounds present in the active compound concentrates according to the invention are less well tolerated by certain crop plants, application techniques may be used in which the application forms prepared using the active compound concentrates are sprayed, with the aid of the spraying equipment, in such a way that as far as possible they do not come into contact with the leaves of the sensitive crop plants, while the active compounds reach the leaves of unwanted plants growing underneath, or the bare soil surface (post-directed, lay-by).

Based on the total amount of active compound, the application rates are, depending on the control target, the season, the target plants and the growth stage, from 0.001 to 3.0, preferably from 0.01 to 1.0, kg of active substance (a.s.)/ha.

To widen the activity spectrum and to achieve synergistic effects, the active compound concentrates may, prior to application, be mixed with numerous representatives of other herbicidal or growth-regulating groups of active compounds and then applied jointly, for example by the tank-mix method. Suitable components for mixtures are, for example, 1,2,4-thiadiazoles, 1,3,4-thiadiazoles, amides, aminophosphoric acid and derivatives thereof, aminotriazoles, anilides, (het)aryloxyalkanoic acid and derivatives thereof, benzoic acid and derivatives thereof, benzothiadiazinones, 2-aroyl-1,3-cyclohexanediones, 2-hetaroyl-1,3-cyclohexanediones, hetaryl aryl ketones, benzylisoxazolidinones, meta-$CF_3$-phenyl derivatives, carbamates, quinolinecarboxylic acid and derivatives thereof, chloroacetanilides, cyclohexenone oxime ether derivatives, diazines, dichloropropionic acid and derivatives thereof, dihydrobenzofurans, dihydrofuran-3-ones, dinitroanilines, dinitrophenols, diphenyl ethers, dipyridyls, halo-carboxylic acids and derivatives thereof, ureas, 3-phenyluracils, imidazoles, imidazolinones, N-phenyl-3,4,5,6-tetrahydrophthalimides, oxadiazoles, oxiranes, phenols, aryloxy- or heteroaryloxyphenoxypropionic esters, phenylacetic acid and derivatives thereof, phenylpropionic acid and derivatives thereof, pyrazoles, phenylpyrazoles, pyridazines, pyridinecarboxylic acid and derivatives thereof, pyrimidyl ethers, sulfonamides, sulfonylureas, triazines, triazinones, triazolinones, triazolecarboxamides and uracils.

It may furthermore be beneficial to mix the active compound concentrates prior to application with other crop protection agents, followed by joint application, for example with agents for controlling pests or phytopathogenic fungi or bacteria. Also of interest is the miscibility with mineral salt solutions, which are employed for treating nutritional and trace element deficiencies. It is also possible to add non-phytotoxic oils and oil concentrates.

The examples below serve to illustrate the invention in more detail and are not to be understood as limitations.

Feedstocks:
- Topramezone (active compound of the formula I, in which $R^1$ and $R^5$ are each methyl, $R^2$ is 4,5-dihydroisoxazol-3-yl, $R^3$ is methylsulfonyl, $R^4$ and $R^6$ are hydrogen);
- Dimethenamid-P
- Emulsifier 1: mixture of calcium dodecylbenzenesulfonate, castor oil ethoxylate, EO/PO triblock copolymer and the phosphate ester of a fatty alcohol having a surfactant content of ≥85% by weight
- Emulsifier 2: EO/PO triblock copolymer having a molecular weight of 6500 and a propylene oxide percentage of 50% by weight
- Emulsifier 3: sodium salt of a phenolsulfonic acid/formaldehyde condensate
- Emulsifier 4: mixture of poly(ethoxylate-co-propoxylates) of tristyrylphenol
- Thickener: xanthan-gum
- Defoamer: commercial polydimethylsiloxane/filler emulsion (Wacker Silikon SRE-PFL) (active content 20% by weight)
- Microbiocide: formulation comprising a mixture of 1,2-benzisothiazolin-3-one and 2-methyl-4-isothiazolin-3-one, active content 5% by weight (Aktizide MBS from Thor Chemie GmbH)
- Hydrocarbon solvent: aromatic hydrocarbon mixture having a content of aromatic compounds of at least 99% by weight and a minimum boiling point, determined according to ASTM 86 to 99, in the range of from 235 to 248° C. and a maximum boiling point in the range of from 290 to 305° C. (Solvesso® 200 from Exxon Mobil)

EXAMPLE 1

Preparation of a Non-Aqueous Active Compound Concentrate

In a stirred tank, 219 g of N-methylpyrrolidone were initially charged, 32 g of topramezone were added and the mixture was stirred until a clear homogeneous mixture was obtained. With stirring, 219 g of hydrocarbon solvent, 32 g of topramezone 538 g of dimethenamid-P/l and 112 g of emulsifier 1 were added in succession, and the mixture was stirred until it was homogeneous. The mixture obtained was a reddish-brown liquid comprising 538 g of dimethenamid-P/l and about 32 g of topramezone/l.

The density, determined at 20° C., was about 1.11 to 1.12 g/cm$^3$. The viscosity, determined using a rotation viscosimeter according to OECD test procedure 114, was about 20 to 35 mPa·s. After two weeks of storage at 54° C., the sample showed no visible changes. The foam height of a 0.3% by weight strength dilution, determined according to Ross-Miles (ASTM-D 1173 53) was not more than 30 mm. The emulsion stability according to CIPAC MT was 36.3.

EXAMPLE 2

Preparation of a Non-Aqueous Active Compound Concentrate

In a stirred tank, 219 g of dimethyl sulfoxide were initially charged, 32 g of topramezone were added and the mixture was stirred until a clear homogeneous mixture was obtained. With stirring, 219 g of hydrocarbon solvent, 32 g of topramezone 538 g of dimethenamid-P/l and 112 g of emulsifier 1 were added in succession, and the mixture was stirred until it was homogeneous. The mixture obtained was a reddish-brown liquid comprising 538 g of dimethenamid-P/l and about 32 g of topramezone/l.

The density, determined at 20° C., was about 1.11 to 1.12 g/cm$^3$. The viscosity, determined using a rotation viscosimeter according to OECD test procedure 114, was about 20 to 35 mPa·s. After two weeks of storage at 54° C., the sample showed no visible changes. The foam height of a 0.3% by weight strength dilution, determined according to Ross-Miles (ASTM-D 1173 53) was not more than 30 mm.

EXAMPLE 3

Preparation of a Non-Aqueous Active Compound Concentrate

In a stirred tank, 219 g of N-methylpyrrolidone were initially charged, 32 g of topramezone were added and the mixture was stirred until a clear homogeneous mixture was obtained. With stirring, 219 g of hydrocarbon solvent, 32 g of topramezone 538 g of dimethenamid-P/l and 112 g of a mixture of calcium dodecylbenzenesulfonate and emulsifier 5 in a weight ratio of 1:1 were added in succession, and the mixture was stirred until it was homogeneous. The mixture obtained was a reddish-brown liquid comprising 538 g of dimethenamid-P/l and about 32 g of topramezone/l.

The density, determined at 20° C., was about 1.11 to 1.12 g/cm$^3$. The viscosity, determined using a rotation viscosimeter according to OECD test procedure 114, was about 20 to 35 mPa·s.

EXAMPLE 4

Preparation of an Aqueous Active Compound Concentrate According to the Invention 1. In a stirred vessel, 400 g of demineralized water were initially charged, and 60 g of 1,2 propylene glycol, 20 g of emulsifier 3 and 166.7 g of an 18% by weight strength aqueous solution of emulsifier 2 were added successively. The mixture was stirred until a homogeneous clear solution was obtained, and 343.9 g of industrial-grade topramezone having a topramezone content of 97.7% by weight and 1 g of defoamer were then added successively. The suspension obtained in this manner was cooled to about 15° C. and then passed through a rotor/stator mill and subsequently, with cooling, through a bead mill until the desired particle size distribution was achieved. In this manner, an aqueous topramezone suspension was obtained in which 80% by weight of the particles had a diameter below 2 μm.

2. In a stirred vessel, 10 g of 1,2-propylene glycol and 119.4 g of demineralized water were initially charged, and 3 g of thickener and then 2 g of the microbiocide were then added successively with stirring. With stirring, the solution obtained in this manner was then added to the suspension obtained in step 1, and a further 4 g of the defoamer were then added with stirring. In this manner, an aqueous suspension was obtained which contained about 336 g of topramezone/l and had a viscosity, determined according OECD 114, of about 60 to 100 mPa·s. The particle size distribution was characterized by a $d_{90}$ of ≤3.5 μm and a $d_{50}$ of ≤1.3 μm.

3. With stirring, 44.4 g of 1,2-propylene glycol, 44.4 g of emulsifier 3 and 66.6 g of a 2% by weight strength aqueous solution of the thickener comprising 1.6% by weight of the biocide to 285.7 g of demineralized water. With stirring, 561 g of dimethenamid-P was added at 23° C. to this solution, and the mixture was stirred until a stable emulsion was obtained. Subsequently, 107.6 g of the suspension obtained in step 2 were added to the emulsion obtained in this manner, and stirring was continued for 10 minutes.

In this manner, an aqueous suspoemulsion was obtained which had a dimethenamid-P content of about 538 g and a topramezone content of about 32 g/l. The density was about 1.11 g/cm$^3$. The viscosity, determined using a rotation viscosimeter according to OECD test procedure 114, was about 70 to 90 mPa·s. The $d_{90}$ was below 7 μm and the $d_{50}$ was below 1.5 μm. The pH of an about 1% by weight strength dilution in demineralized water was in the range of from about 2.5 to 4.5.

The invention claimed is:

1. A non-aqueous active compound concentrate comprising
    a) from 10 to 100 g/l of at least one 4-benzoyl-substituted pyrazole compound of the formula I or one of its salts

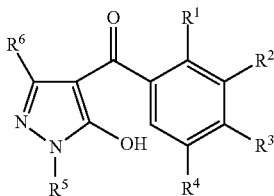

in which $R^1$ and $R^5$ are each methyl; $R^3$ is methylsulfonyl; $R^2$ is 4,5-dihydroisoxazol-3-yl; and $R^4$ and $R^6$ are hydrogen, b) from 400 to 700 g/l of 2-chloro-N-(2,4-dimethyl-3-thienyl)-N-(2-methoxy-1-methylethy)acetamide, and c) from 10 to 200 g/l of at least one surfactant S selected from a mixture of at least one anionic surfactant and at least one nonionic surfactant, where the components a), b) and c) are present dissolved in a mixture of organic solvents containing at least 95% by weight, based on the solvent mixture, of d1) at least one aprotic polar organic solvent having a miscibility with water at 25° C. and 1 bar of at least 50 g/l, which is selected from the group consisting of dimethyl sulfoxide, N-methylpyrrolidone, N-ethylpyrrolidone, and mixtures thereof, and d2) at least one organic solvent having a solubility in water at 25° C. and 1 bar of less than 5 g/l, which is a hydrocarbon solvent;

in which the anionic surfactant is selected from the group consisting of compounds comprising at least one $SO_3$ group or one $PO_4$ group and at least one aliphatic hydrocarbon radical having 8 to 22 carbon atoms or an araliphatic hydrocarbon radical having 10 to 24 carbon atoms and in which the nonionic surfactant comprises, as main component, at least one poly-$C_2$-$C_3$-alkylene glycol ether compound, where the weight ratio of apolar protic solvent to hydrocarbon solvent is from 1:10 to 10:1, and where the total amount of organic solvent is from 300 to 600 g/l.

2. The active compound concentrate according to claim 1, wherein the organic solvent has a solubility in water at 25° C. and 1 bar of less than 5 g/l is a hydrocarbon solvent and in which the weight ratio of aprotic polar solvent to hydrocarbon solvent is in the range of from 5:1 to 1:5.

3. The non-aqueous active compound concentrate of claim 1 in which the concentration of the at least one 4-benzoyl-substituted pyrazole compound of the formula I or its salt is from 20 to 100 g/l.

4. The non-aqueous active compound concentrate of claim 1 in which the concentration of the at least one 4-benzoyl-substituted pyrazole compound of the formula I or its salt is from 20 to 50 g/l.

5. The non-aqueous active compound concentrate of claim 1 in which the concentration of the 2-chloro-N-(2,4-dimethyl-3-thienyl)-N-(2-methoxy-1-methylethyl)acetamide is from 400 to 600 g/l.

6. The non-aqueous active compound concentrate of claim 4 in which the concentration of the 2-chloro-N-(2,4-dimethyl-3-thienyl)-N-(2-methoxy-1-methylethyl)acetamide is from 400 to 600 g/l.

7. The non-aqueous active compound concentrate of claim 1 wherein the aprotic polar organic solvent is N-methylpyrrolidone.

8. The non-aqueous active compound concentrate of claim 4 wherein the aprotic polar organic solvent is N-methylpyrrolidone.

9. A method for controlling unwanted vegetation which comprises preparing an aqueous spray liquor by diluting an active compound concentrate according to claim 1 and applying the spray liquor to act on plants, their seeds and/or their habitat and allowing the spray liquor to act on plants, their seeds and/or their habitat.

10. The method according to claim 9 which comprises treating the leaves of the unwanted plants with the aqueous spray liquor.

* * * * *